(12) United States Patent  
Sugimoto et al.

(10) Patent No.: US 8,466,956 B2  
(45) Date of Patent: Jun. 18, 2013

(54) SCANNING ENDOSCOPE PROCESSOR AND SCANNING ENDOSCOPE APPARATUS

(75) Inventors: Hideo Sugimoto, Tokyo (JP); Kohei Iketani, Saitama (JP)

(73) Assignee: Hoya Corporation, Tokyo (JP)

( * ) Notice: Subject to any disclaimer, the term of this patent is extended or adjusted under 35 U.S.C. 154(b) by 729 days.

(21) Appl. No.: 12/640,080

(22) Filed: Dec. 17, 2009

(65) Prior Publication Data

US 2010/0157036 A1    Jun. 24, 2010

(30) Foreign Application Priority Data

Dec. 19, 2008    (JP) ................................ 2008-324225

(51) Int. Cl.
*A62B 1/04* (2006.01)
*G02B 6/06* (2006.01)
*A61B 1/06* (2006.01)

(52) U.S. Cl.
USPC ............... 348/65; 348/45; 385/117; 385/118; 385/119; 600/173; 600/478

(58) Field of Classification Search
USPC .......................................................... 348/65
See application file for complete search history.

(56) References Cited

U.S. PATENT DOCUMENTS

| 5,415,158 | A | * | 5/1995 | Barthel et al. ................ 600/149 |
| 5,951,461 | A | * | 9/1999 | Nyo et al. ..................... 600/118 |
| 6,294,775 | B1 | * | 9/2001 | Seibel et al. ............... 250/208.1 |
| 6,845,190 | B1 | | 1/2005 | Smithwick et al. |
| 6,975,898 | B2 | | 12/2005 | Seibel |
| 7,129,472 | B1 | | 10/2006 | Okawa et al. |
| 7,159,782 | B2 | * | 1/2007 | Johnston et al. ......... 235/462.45 |
| 7,252,236 | B2 | * | 8/2007 | Johnston et al. ......... 235/462.32 |
| 7,298,938 | B2 | * | 11/2007 | Johnston ........................ 385/25 |
| 7,312,879 | B2 | * | 12/2007 | Johnston ....................... 356/614 |
| 7,530,948 | B2 | | 5/2009 | Seibel et al. |
| 7,608,842 | B2 | | 10/2009 | Johnson |
| 7,616,986 | B2 | | 11/2009 | Seibel et al. |
| 8,212,884 | B2 | * | 7/2012 | Seibel et al. ............... 348/220.1 |
| 2004/0254474 | A1 | | 12/2004 | Seibel et al. |
| 2006/0195014 | A1 | | 8/2006 | Seibel et al. |

(Continued)

FOREIGN PATENT DOCUMENTS

| JP | 2001-174744 | 6/2001 |
| JP | 3943927 | 4/2007 |

(Continued)

OTHER PUBLICATIONS

Japan Office action, dated Jan. 22, 2013 along with an english translation thereof.

*Primary Examiner* — Backhean Tiv

(74) *Attorney, Agent, or Firm* — Greenblum & Bernstein, P.L.C.

(57) ABSTRACT

A scanning endoscope processor, comprising a photoelectric converter and a controller, is provided. The scanning endoscope processor controls a scanning endoscope having first and second transmitters and an actuator. The photoelectric converter receives light transmitted from the second transmitter and generates a pixel signal according to the amount of light received. The second transmitter transmits reflected light and/or fluorescence from a point within an observation area illuminated by the light emitted from a first emission end. The first transmitter emits the light as a beam from the first emission end. The actuator moves the first emission end along a spiral course. The controller adjusts at least one of a first angular velocity and a generation cycle so that the product of the first angular velocity, the generation cycle, and a first distance is within a predetermined range.

5 Claims, 10 Drawing Sheets

U.S. PATENT DOCUMENTS

| | | | |
|---|---|---|---|
| 2006/0226231 A1* | 10/2006 | Johnston et al. | 235/462.45 |
| 2007/0035797 A1 | 2/2007 | Kanai | |
| 2007/0299309 A1 | 12/2007 | Seibel et al. | |
| 2008/0265178 A1 | 10/2008 | Johnson | |
| 2010/0103095 A1* | 4/2010 | Yamamoto et al. | 345/156 |
| 2010/0103100 A1* | 4/2010 | Yamamoto | 345/158 |

FOREIGN PATENT DOCUMENTS

| | | |
|---|---|---|
| JP | 2008-504557 | 2/2008 |
| JP | 2008-514342 | 5/2008 |
| JP | 2008-531193 | 8/2008 |
| WO | 2008/133636 | 11/2008 |

* cited by examiner

SPIRAL COURSE

SCANNING ENDOSCOPE PROCESSOR AND SCANNING ENDOSCOPE APPARATUS

BACKGROUND OF THE INVENTION

1. Field of the Invention

The present invention relates to a scanning endoscope processor that reduces the generation of image signals not being used.

2. Description of the Related Art

Japanese Patent No. 3943927 discloses a scanning endoscope. In a general scanning endoscope, light for illumination is transmitted through an optical fiber from a stationary incident end to a movable emission end and a scanning operation is carried out by successively moving the emission end of the optical fiber.

In order to successively move the emission end in a stable manner, the emission end is rotated about a starting point for the movement as the radius between the starting point and the emission end increases, i.e., the emission end is moved along a spiral course. In addition, to maintain ease of control the angular velocity of the rotating emission end is kept constant. The generation cycle, which is a cycle for generating pixel signals, is also held constant.

However, by keeping the angular velocity and the generation cycle constant, the number of generated pixels signals per a predetermined area increases as the emission end is moved farther from the center of the spiral course (i.e. the starting point). On the other hand, the number of pixel signals per a predetermined area required for display on a monitor is constant regardless of the distance between the center of the spiral course and the emission end. Accordingly, even though more pixel signals than the number required to produce an image are generated, a portion of the generated pixel signals are deleted without being used. This situation is problematic because power is needlessly consumed in the generation of pixel signals that will not be used.

SUMMARY OF THE INVENTION

Therefore, an object of the present invention is to provide a scanning endoscope processor that enables a reduction in power consumption by controlling a scanning endoscope more adequately.

According to the present invention, a scanning endoscope processor, comprising a photoelectric converter and a controller, is provided. The scanning endoscope processor controls a scanning endoscope having a first transmitter, an actuator, and a second transmitter. The photoelectric converter receives light transmitted from the second transmitter and generates a pixel signal according to the amount of light received. The second transmitter transmits reflected light and/or fluorescence from a point within an observation area illuminated by the light emitted from a first emission end. The first transmitter transmits light from a first incident end to the first emission end. The first transmitter emits the light as a beam from the first emission end. The actuator moves the first emission end along a spiral course. The controller adjusts at least one of a first angular velocity and a generation cycle so that the product of the first angular velocity, the generation cycle, and a first distance is within a predetermined range. The second emission end is moved at the first angular velocity along the spiral course. The generation cycle is a cycle for generating the pixel signal. The first distance is a distance between the position of the second emission end on the spiral course and the center of the spiral course.

According to the present invention, a scanning endoscope apparatus, comprising a first transmitter, an actuator, a second transmitter, a photoelectric converter, and a controller, is provided. The first transmitter transmits light from a first incident end to the first emission end. The first transmitter emits the light as a beam from the first emission end. The actuator moves the first emission end along a spiral course. The second transmitter transmits reflected light and/or fluorescence from a point within an observation area illuminated by the light emitted from a first emission end. The photoelectric converter receives the light transmitted from the second transmitter and generates a pixel signal according to the amount of the light received. The controller adjusts at least one of a first angular velocity and a generation cycle so that the product of the first angular velocity, the generation cycle, and a first distance is within a predetermined range. The second emission end is moved at the first angular velocity along the spiral course. The generation cycle is a cycle for generating the pixel signal. The first distance is a distance between the position of the second emission end on the spiral course and the center of the spiral course.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
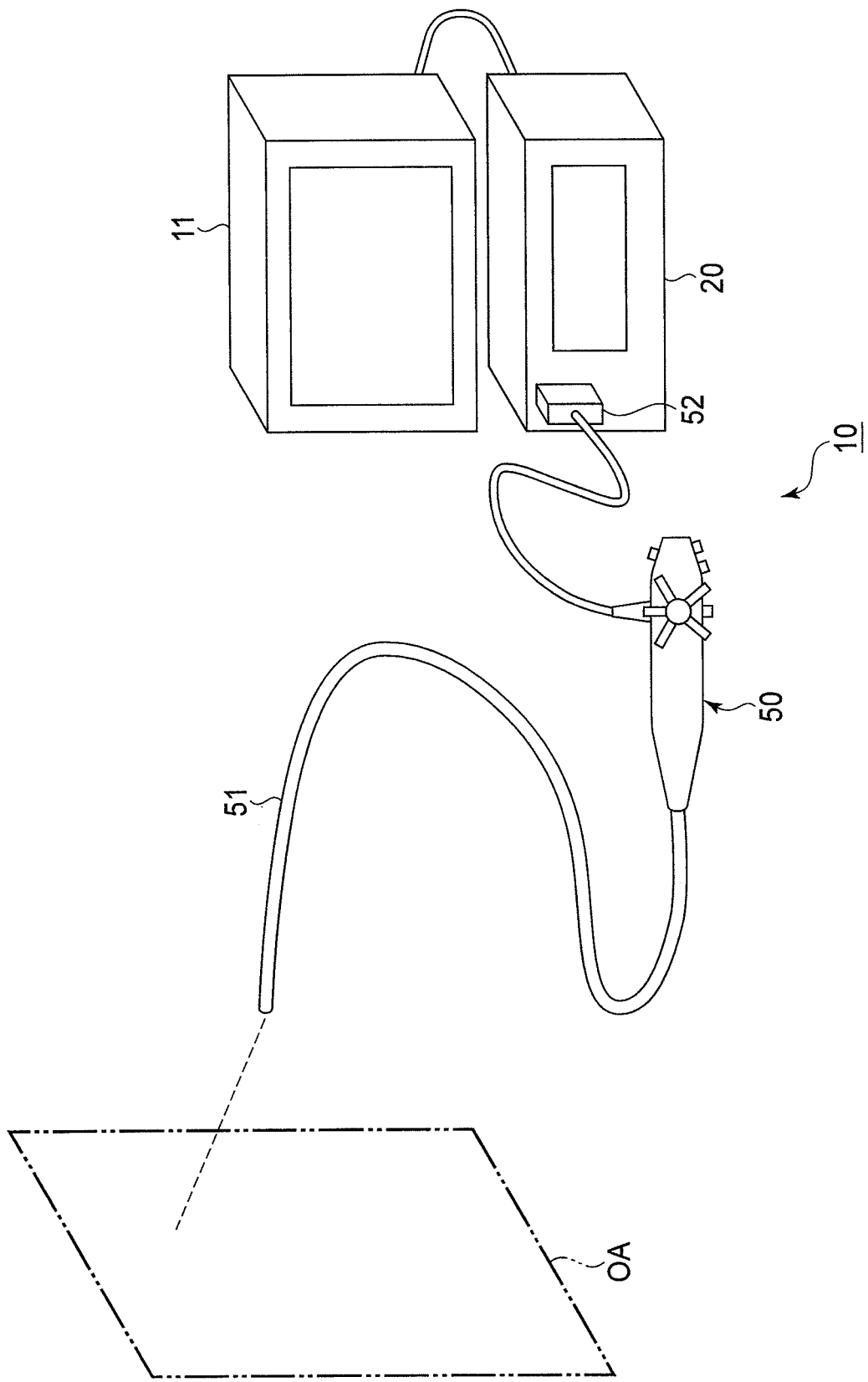
FIG. 1 is a schematic illustration of a scanning endoscope apparatus having a scanning endoscope processor of the embodiment of the present invention.

The present invention is described below with reference to the embodiment shown in the drawings.

In FIG. 1, the scanning endoscope apparatus 10 comprises a scanning endoscope processor 20, a scanning endoscope 50, and a monitor 11. The scanning endoscope processor 20 is connected to the scanning endoscope 50 and the monitor 11.

Hereinafter, an emission end of an illumination fiber ("first emission end" not depicted in FIG. 1) and incident ends of image fibers (not depicted in FIG. 1) are mounted in the distal end of the insertion tube 51 of the scanning endoscope 50. In addition, an incident end of the illumination fiber (first incident end) and emission ends of the image fibers are mounted to a connector 52 that connects to the scanning endoscope processor 20.

The scanning endoscope processor 20 provides light that is shined on an observation area (see "OA" in FIG. 1). The light emitted from the scanning endoscope processor 20 is transmitted to the distal end of the insertion tube 51 through the illumination fiber (first transmitter), and is directed towards one point on the observation area. Reflected light and/or autofluorescence from the illuminated point is transmitted from the distal end of the insertion tube 51 to the scanning endoscope processor 20.

The direction of the emission end of the illumination fiber is changed by a fiber actuator (not depicted in FIG. 1). By changing the direction, the observation area is scanned with the light emitted from the illumination fiber. The fiber actuator is controlled by the scanning endoscope processor 20.

The scanning endoscope processor 20 receives reflected light and/or autofluorescence that is scattered from the illuminated point, and generates a pixel signal according to the amount of light received. One frame of an image signal is generated by generating pixel signals corresponding to the illuminated points dispersed throughout the observation area. The generated image signal is transmitted to the monitor 11, where an image corresponding to the received image signal is displayed.

Figure 2:
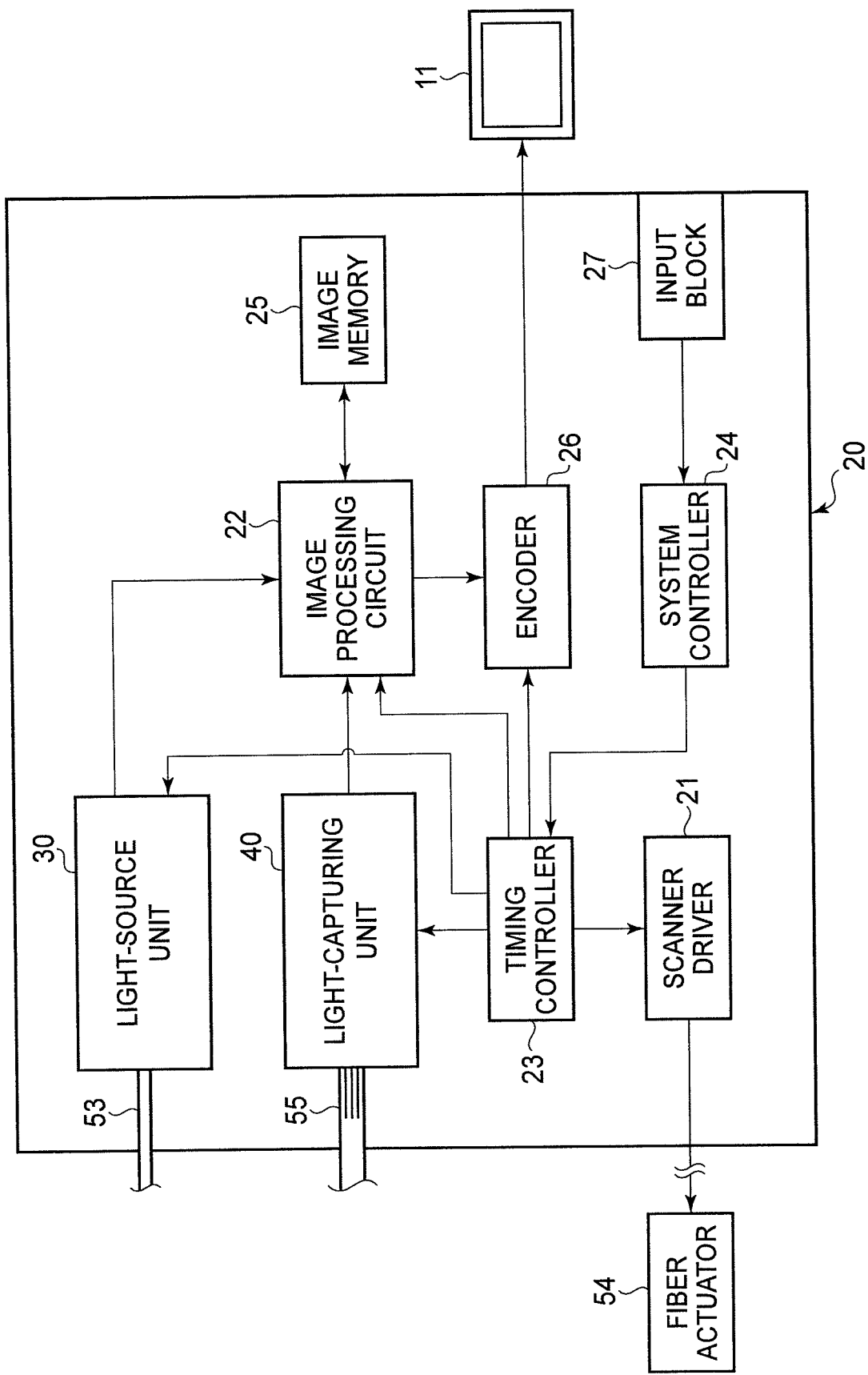
FIG. 2 is a block diagram schematically showing the internal structure of the scanning endoscope processor of the scanning endoscope.

As shown in FIG. 2, the scanning endoscope processor 20 comprises a light-source unit 30, a light-capturing unit 40, a scanning driver 21, an image processing circuit 22, a timing controller 23 (controller), a system controller 24, and other components.

The light-source unit 30 comprises red, green, and blue lasers (not depicted) that emit red, green, and blue laser beams, respectively. A white laser beam is emitted from the light-source unit 30 by mixing the red, green, and blue laser beams.

The light-source unit 30 provides the illumination fiber 53 with the white laser beam. The scanning driver 21 controls the fiber actuator 54 to move the emission end of the illumination fiber 53 along a spiral course as described later.

The light reflected from the illuminated point in the observation area is transmitted to the scanning endoscope processor 20 by the image fibers 55 mounted in the scanning endoscope 50. The transmitted light is made incident on the light-capturing unit 40.

The light-capturing unit 40 generates a pixel signal according to the amount of incident light. The pixel signal is transmitted to the image processing circuit 22, which stores the received pixel signal in the image memory 25. Once pixel signals corresponding to the illuminated points dispersed throughout the observation area have been stored, the image processing circuit 22 carries out predetermined image processing on the pixel signals, and then one frame of the image signal, which pixel signals constitute, is transmitted to the monitor 11 via the encoder 26.

By connecting the scanning endoscope 50 to the scanning endoscope processor 20, optical connections are made between the light-source unit 30 and the illumination fiber 53 mounted in the scanning endoscope 50, and between the light-capturing unit 40 and the image fibers 55. In addition, by connecting the scanning endoscope 50 to the scanning endoscope processor 20, the fiber actuator 54 mounted in the scanning endoscope 50 is electrically connected to the scanning driver 21.

The timing for carrying out the operations of the light-source unit 30, the light-capturing unit 40, the image processing circuit 22, the scanning driver 21, and the encoder 26 is controlled by the timing controller 23. In addition, the timing controller 23 and other components of the scanning endoscope apparatus 10 are controlled by the system controller 24. The scanning endoscope processor 20 comprises an input block 27 that comprises a front panel (not depicted) and other mechanisms. A user can input certain commands to the input block 27. The system controller 24 controls the components on the basis of the input commands.

Figure 3:
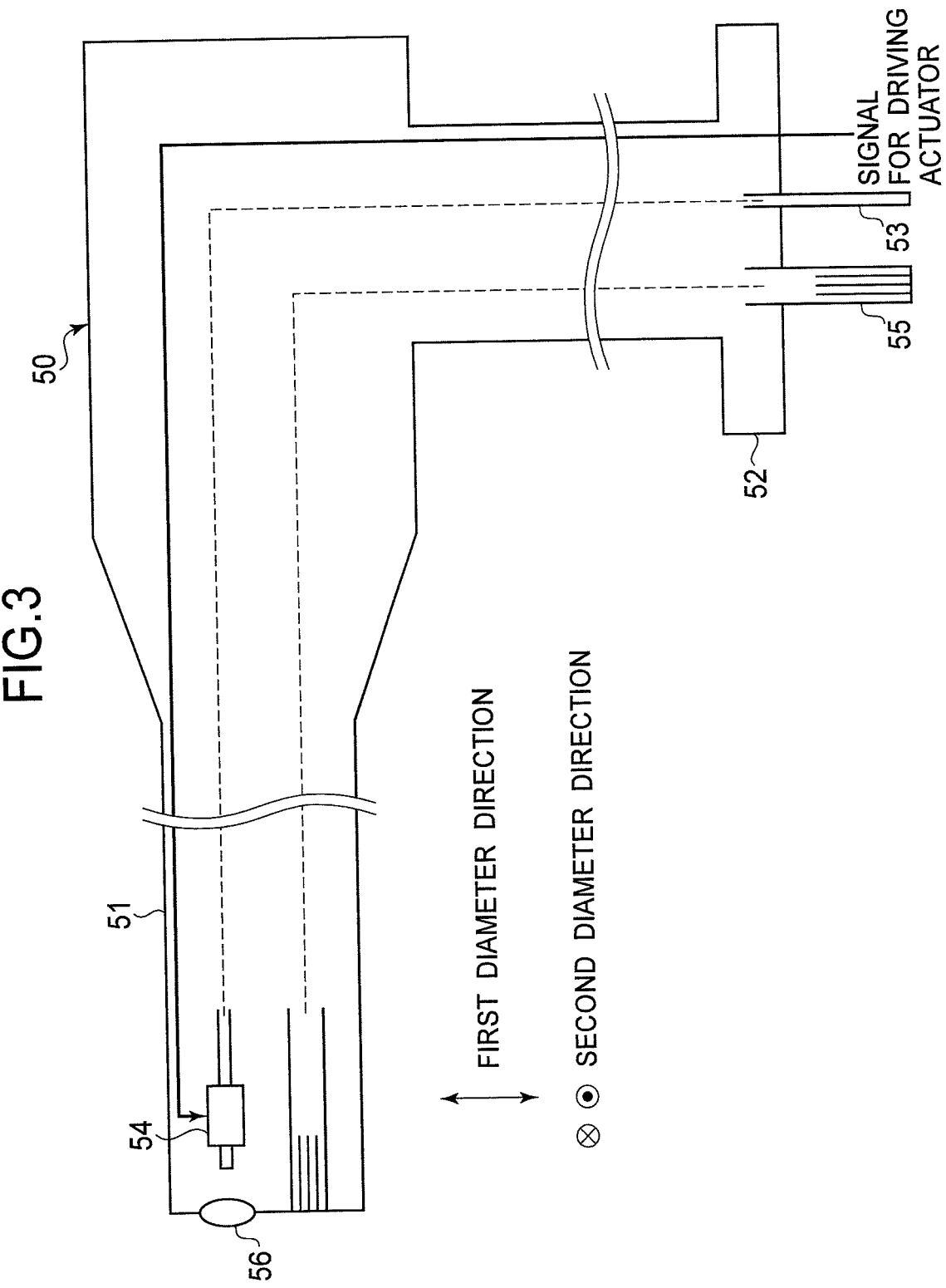
FIG. 3 is a block diagram schematically showing the internal structure of the scanning endoscope.

Next, the structure of the scanning endoscope 50 is explained. As shown in FIG. 3, the scanning endoscope 50 comprises the illumination fiber 53, the fiber actuator 54, the image fibers 55, a condenser lens 56, and other components.

The illumination fiber 53 and the image fibers 55 are mounted from the connector 52 to the distal end of the insertion tube 51 inside of the scanning endoscope 50. As described above, the white laser beam emitted by the light-source unit 30 is incident on the incident end of the illumination fiber 53. The incident white laser beam is transmitted to the emission end of the illumination fiber 53.

The fiber actuator 54 is mounted near the emission end of illumination fiber 53. The fiber actuator 54 comprises piezoelectric elements (not depicted). The piezoelectric elements deflect the illumination fiber 53 in the first and second diameter directions of the illumination fiber 53. The first and second diameter directions are perpendicular to each other and perpendicular to the axial direction of the emission end of the illumination fiber 53.

Figure 4:
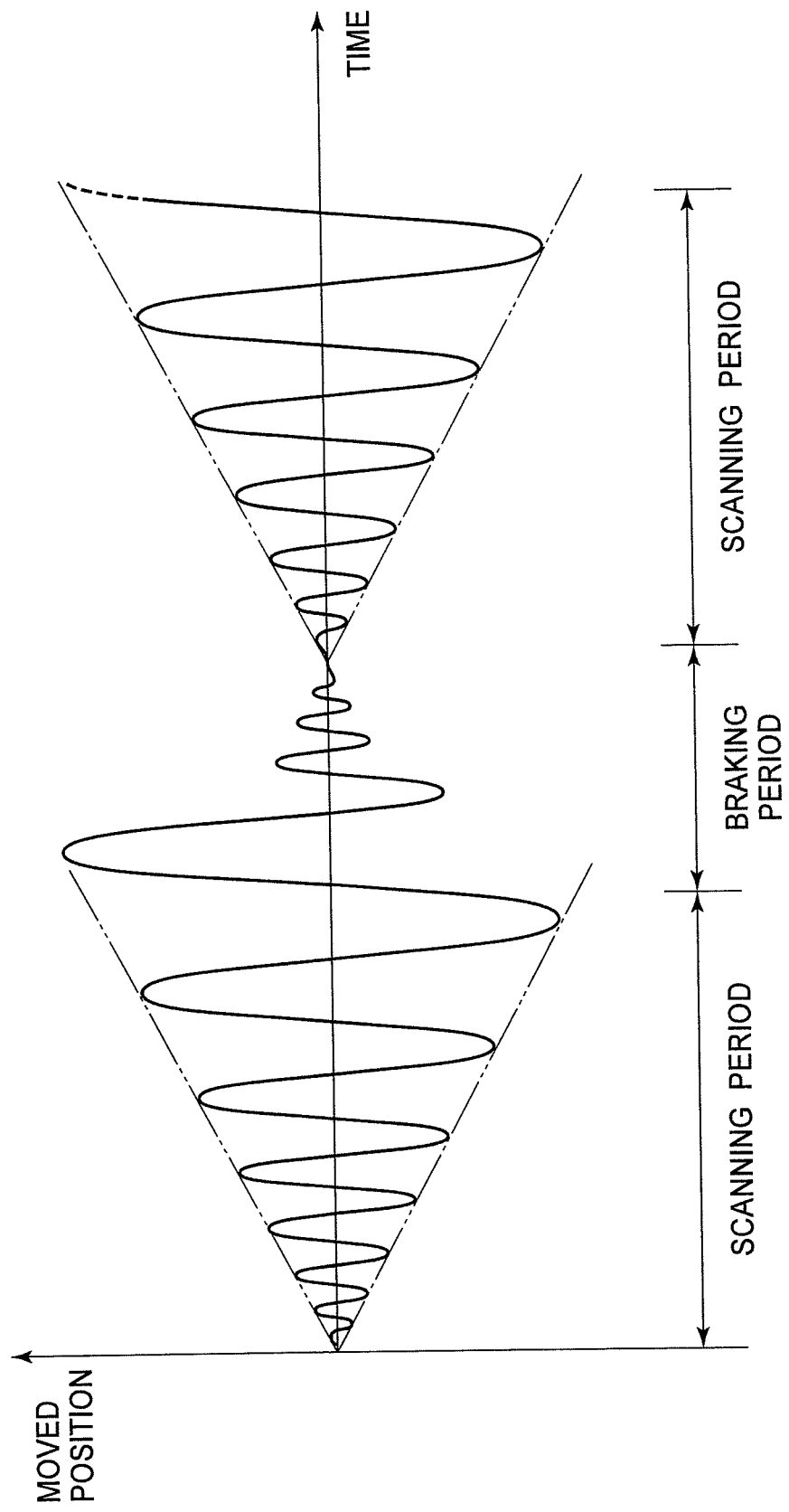
FIG. 4 is a graph illustrating the change in position of the emission end from the standard point along the first and second diameter directions.

As shown in FIG. 4, the emission end of the illumination fiber 53 is moved so that the emission end vibrates along the first and second diameter directions at amplitudes that are repetitively increased and decreased. The frequencies of the vibration along the first and second diameter directions are adjusted to be equal. In addition, the period to increase and to decrease the amplitudes of the vibration along the first and second diameter directions are synchronized. Further, the phase of the vibration along the first and second diameter directions is shifted by 90 degrees.

Figure 5:
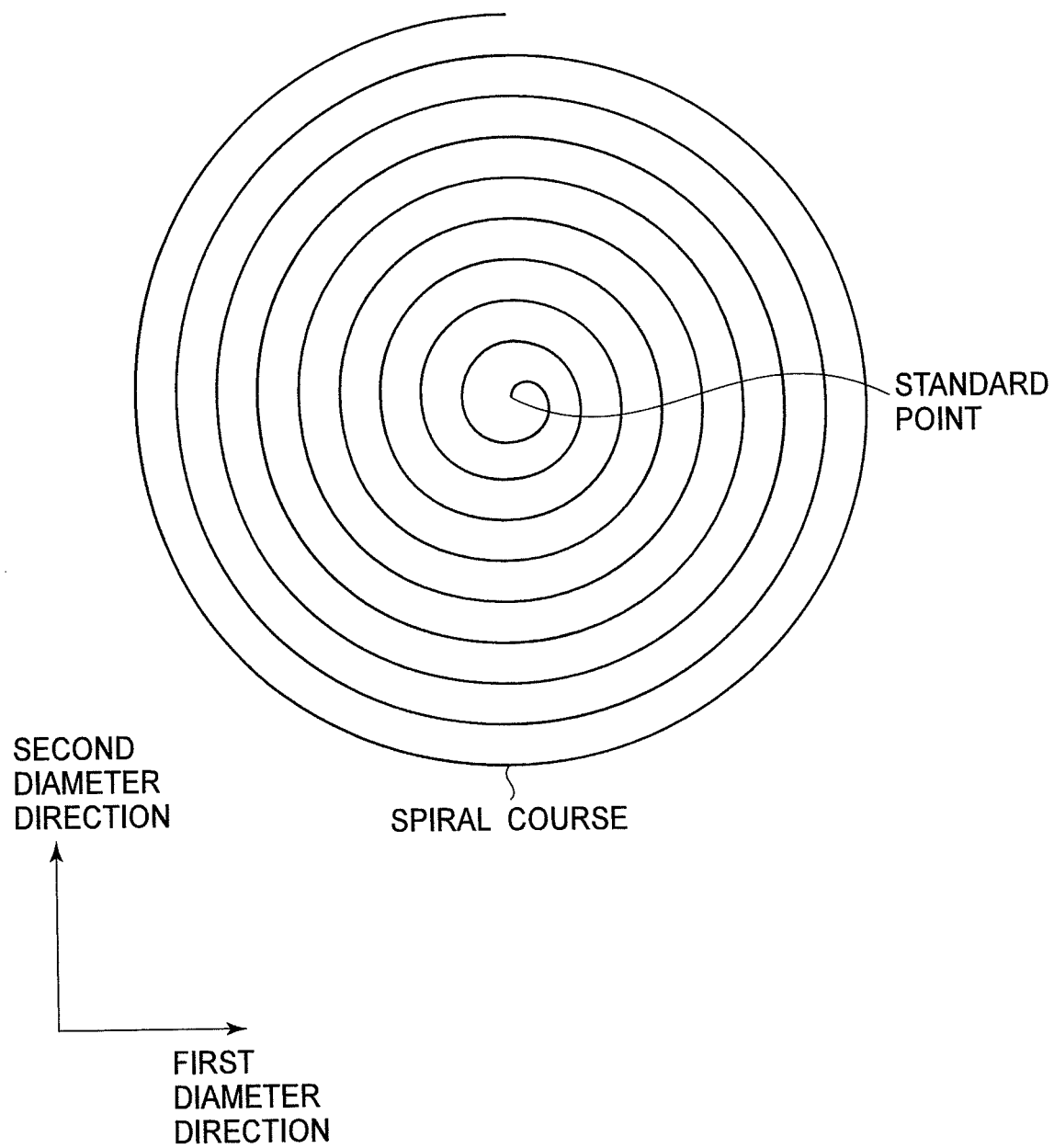
FIG. 5 is an illustration of a spiral course along which the emission end of the illumination fiber is moved by the fiber actuator.

By vibrating the emission end of the illumination fiber 53 along the first and second diameter directions as described above, the emission end is rotated at a constant angular velocity as the radius is repetitively increased and decreased. And the emission end traces the spiral course shown in FIG. 5, and the observation area is scanned with the white laser beam.

The position of the emission end of the illumination fiber 53 when it is not deflected is defined as a standard point. While the emission end is vibrated with increasing amplitude starting from the standard point (see "scanning period" in FIG. 4), illumination of the observation area with the white laser beam and generation of pixel signals are carried out.

In addition, when the amplitude reaches a maximum among the predetermined range, one scanning operation for producing one image terminates. After termination of a scanning operation, the emission end of the illumination fiber 53 is returned to the standard point by vibration of the emission end along the first and second diameter directions at decreasing amplitudes (see "braking period" in FIG. 4). When the emission end is moved to the standard point, it is at the beginning of a scanning operation for generating another image.

The condenser lens 56 is mounted downstream—in the direction of emission of the white laser beam—from the emission end of the illumination fiber 53 when the emission end is positioned at the standard point. The condenser lens 56 is fixed on the scanning endoscope so that the optical axis of the condenser lens 56 is parallel to the luminous flux of the white laser beam emitted from the emission end of the illumination fiber 53 when the emission end is positioned at the standard point.

Figure 6:
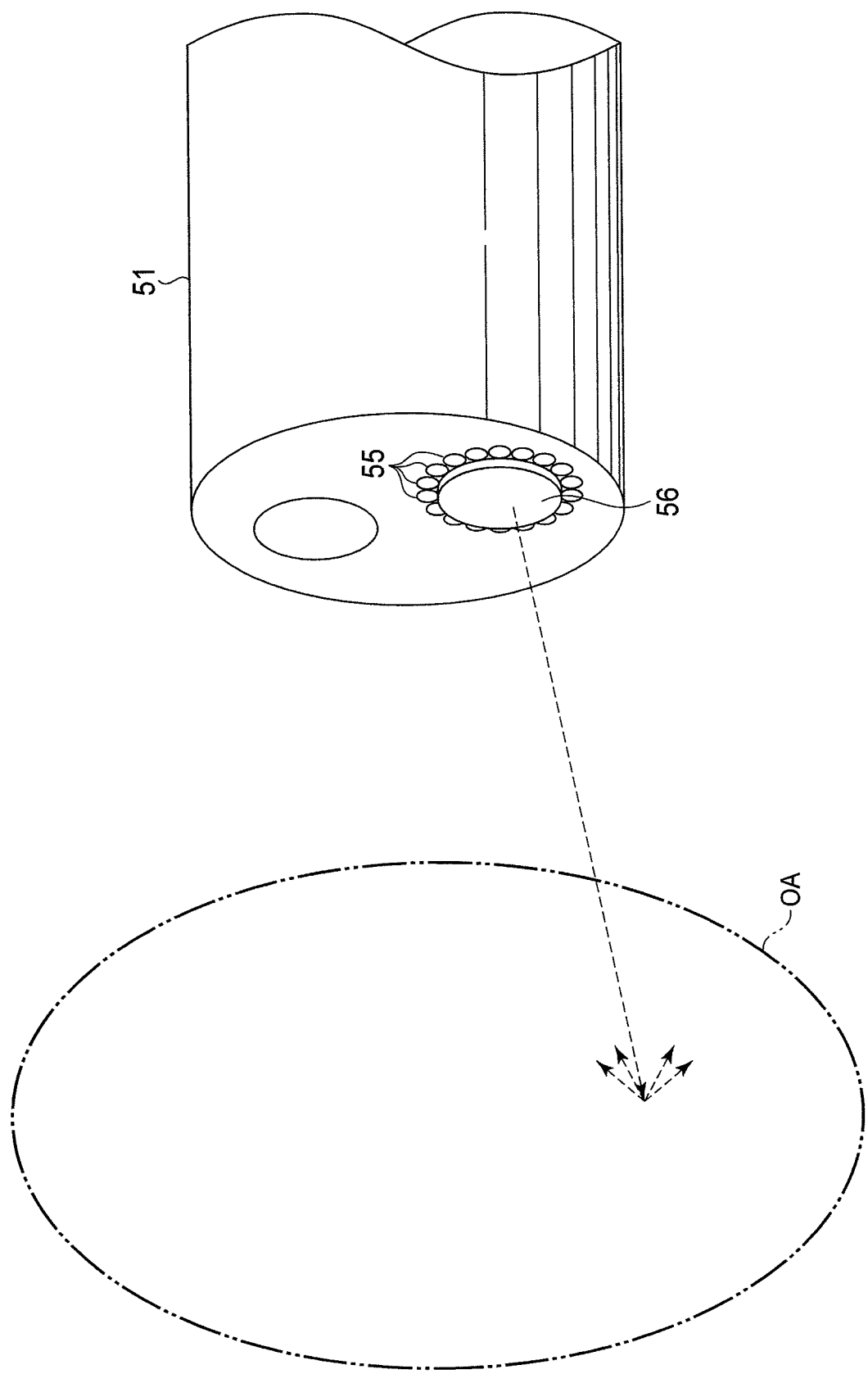
FIG. 6 is an illustration of the white laser beam emitted from the condenser lens.

The white laser beam emitted from the illumination fiber 53 passes through the condenser lens 56 and travels toward one point within the observation area (see FIG. 6). The reflected light is scattered from the point illuminated by the white laser beam. The scattered, reflected light is incident on the incident ends of the image fibers 55.

A plurality of image fibers 55 are mounted in the scanning endoscope 50. The incident ends of the image fibers 55 are arranged around the condenser lens 56 (see FIG. 6). The light that is scattered and reflected from the point in the observation area is incident on all the image fibers 55.

The reflected light incident on the incident ends of the image fibers 55 is transmitted to the emission end. As described above, the emission ends of the image fibers 55 are optically connected to the light-capturing unit 40. Therefore, the reflected light transmitted to the emission end is incident on the light-capturing unit 40.

Figure 7:
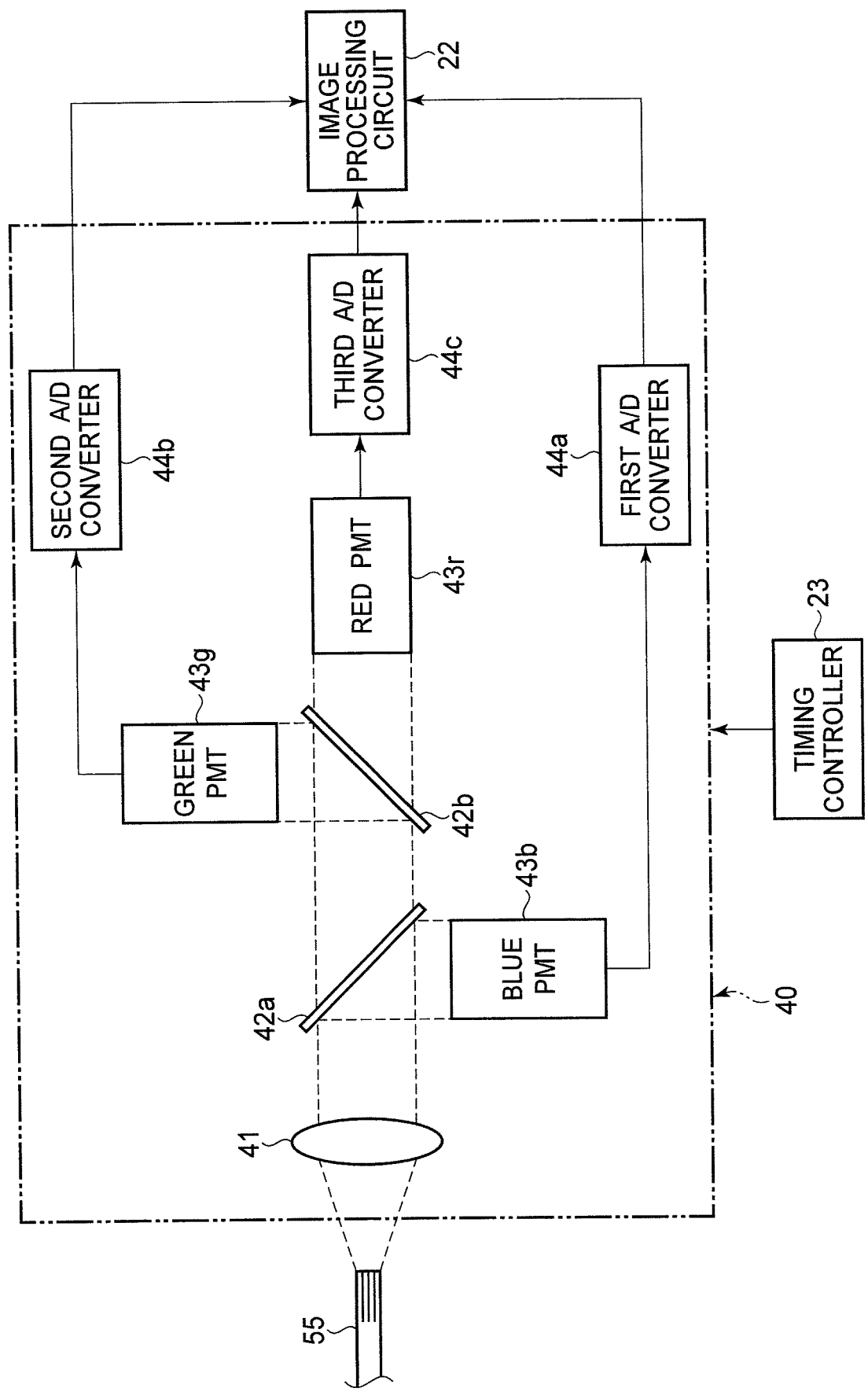
FIG. 7 is a block diagram schematically showing the internal structure of the light-capturing unit.

As shown in FIG. 7, the light-capturing unit 40 comprises a collimating lens 41, first and second beam splitters 42a and 42b, red, green, and blue photomultiplier tubes (PMTs) 43r, 43g, and 43b, and first to third A/D converters 44a to 44c.

The collimating lens 41 and the first and second beam splitters 42a and 42b are arranged in the emitting direction of the emission ends of the image fibers 55. The light incident from the bundle of a plurality of image fibers 55 passes through the collimating lens 41 before arriving at the first beam splitter 42a.

The first beam splitter 42a is inclined against the light incident from the collimating lens 41, and reflects a blue light component so that the reflected blue light component is made incident on the blue PMT 43b. In addition, the first beam splitter 42a transmits the bands of light excluding the band of the blue light component, and lets the transmitted light reach the second beam splitter 42b.

The second beam splitter 42b is inclined against the light passing through the first beam splitter 42a, and reflects a green light component so that the reflected green light component is made incident on the green PMT 43g. In addition, the second beam splitter 42b transmits the bands of light excluding the band of the green light component, so that the transmitted light is incident on the red PMT 43r.

The red, green, and blue PMTs 43r, 43g, and 43b generate pixel signals according to the amounts of the red, green, and blue light components of the reflected light that are scattered from the point of illumination within the observation area and transmitted by the image fibers 55.

The pixel signals generated by the blue, green, and red PMTs 43b, 43g, and 43r are digitized by the first, second, and third A/D converters 44a, 44b, and 44c, respectively. The digitized pixel signals are transmitted to the image processing circuit 22.

The first to third A/D converters 44a to 44c are controlled by the timing controller 23. On the basis of the control of the timing controller 23, the cycle of the analog-to-digital (A/D) conversion processing is adjusted. By adjusting the cycle of the A/D conversion processing, the cycle for generating the digitized pixel signals (generation cycle) is adjusted.

The cycle for generating the digitized pixel signals is adjusted according to the position of the moved emission end of the illumination fiber 53. As described above, the emission end is rotated at a constant angular velocity. The cycle of the A/D conversion processing of the first to third A/D converters 44a-44c is adjusted by the timing controller 23 so that the cycle is inversely proportional to the distance between the standard point and the position of the emission end (first distance), i.e., so that the product obtained from multiplying the cycle by the distance is constant.

The image processing circuit 22 receives a timing signal necessary for controlling the scanning driver 21 that is also transmitted from the timing controller 23. The image processing circuit 22 estimates the point where the white laser beam is shone on the basis of the timing signal, and stores the pixel signals at the address of the image memory 25 corresponding to the estimated point.

As described above, the observation area is scanned with the white laser beam, pixel signals are generated on the basis of the reflected light at the respective points illuminated by the white light beam, and the generated pixel signals are stored at the addresses corresponding to the points. The image signal corresponding to the entire observation area comprises the pixel signals corresponding to the individual points from the scan-start point to the scan-end point.

In the above embodiment, pixel signals that are not needed in the production of an image are not generated. The effect is explained in detail below.

As described above, the emission end of the illumination fiber 53 is moved at the constant angular velocity "ω" along the spiral course. Accordingly, when the distance between the emission end and the standard point is "r", the moving velocity of the emission end is calculated by the equation "r×ω".

Figure 8:
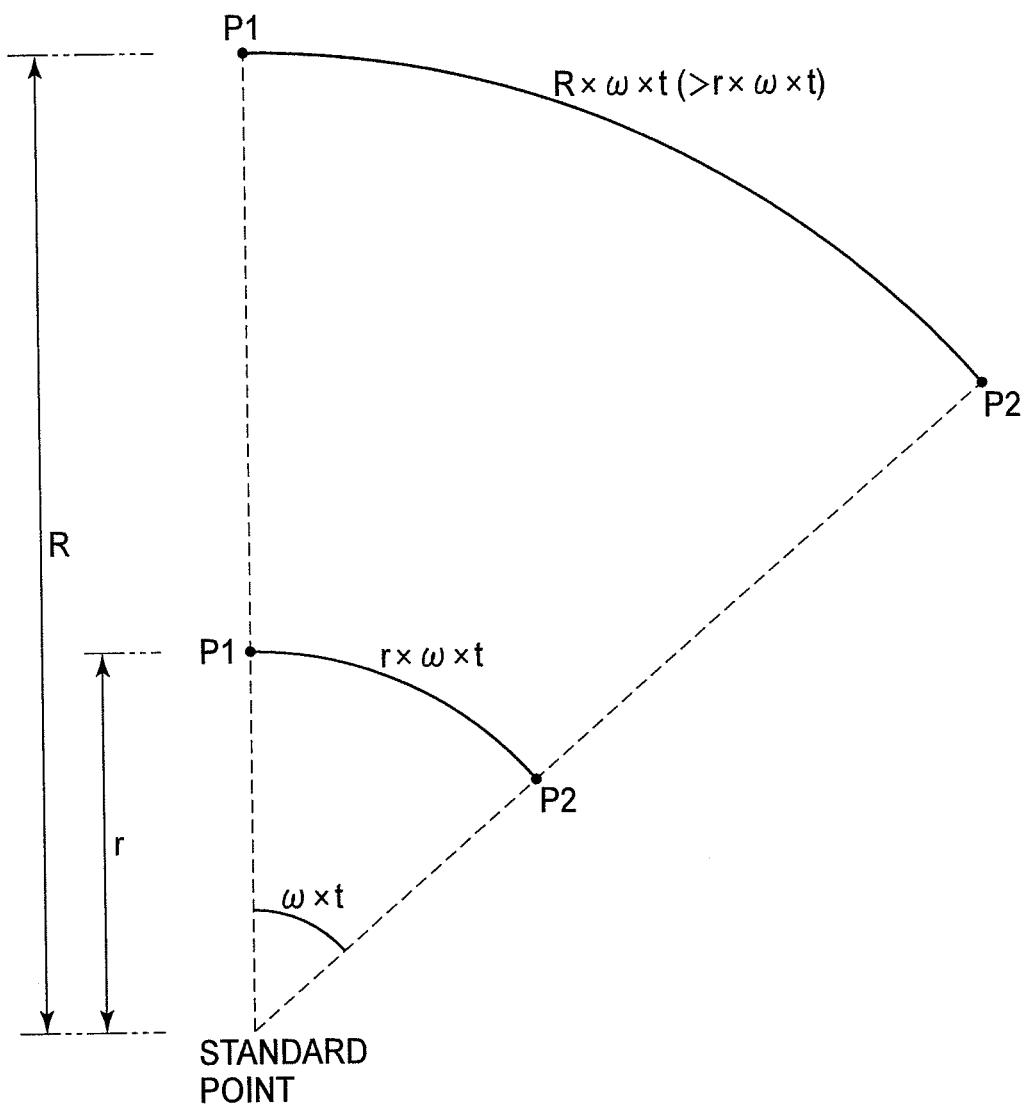
FIG. 8 is an illustration of the space between the neighboring sampling points.

If the A/D conversion cycle is "t", a space between the neighboring sampling points where the neighboring digitized pixel signals are generated (see "P1" and "P2" in FIG. 8) is calculated by the equation "r×ω×t".

Figure 9:
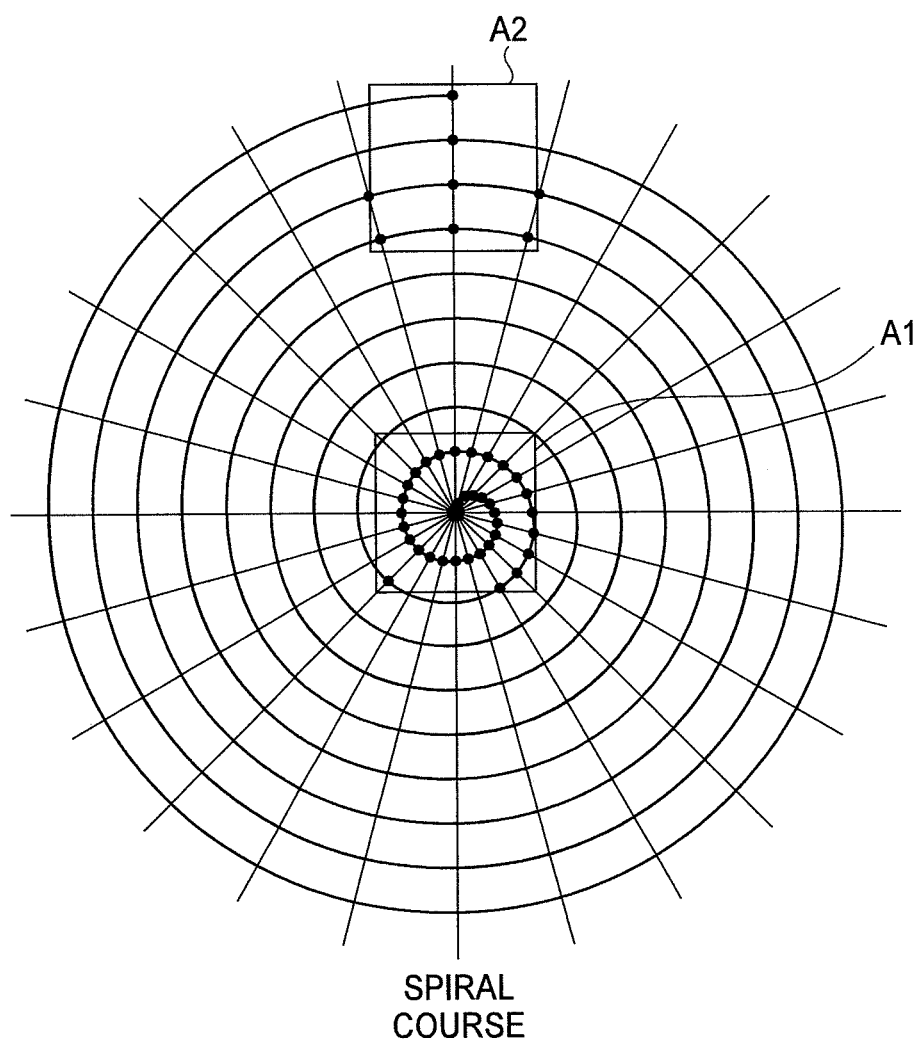
FIG. 9 is a conceptual illustration of the generation cycle of the pixel signals under the provision that the angular velocity and the A/D conversion cycle are kept constant.

If the A/D conversion cycle is constant, as in a general scanning endoscope processor, the space between the neighboring sampling points becomes greater as the emission end is moved farther from the standard point, due to the constant angular velocity. Accordingly, as shown in FIG. 9, a generation density (see black dots), which is a density of generated pixel signals per a certain-sized area, is relatively larger in a first area (see "A1") that is near the standard point. On the other hand, the generation density is relatively smaller in a second area (see "A2") that is farther away from the standard point.

Accordingly, if the A/D conversion cycle is constant, the cycle is predetermined so that pixel signals can be stored for all the addresses of the image memory 25 corresponding to the area farthest from the standard point. However, if the constant A/D conversion cycle is predetermined according to the above manner, the number of digitized pixel signals generated for an area near the standard point will exceed the number of the corresponding addresses. When this occurs, unnecessary pixel signals are deleted without being stored in the image memory 25.

Figure 10:
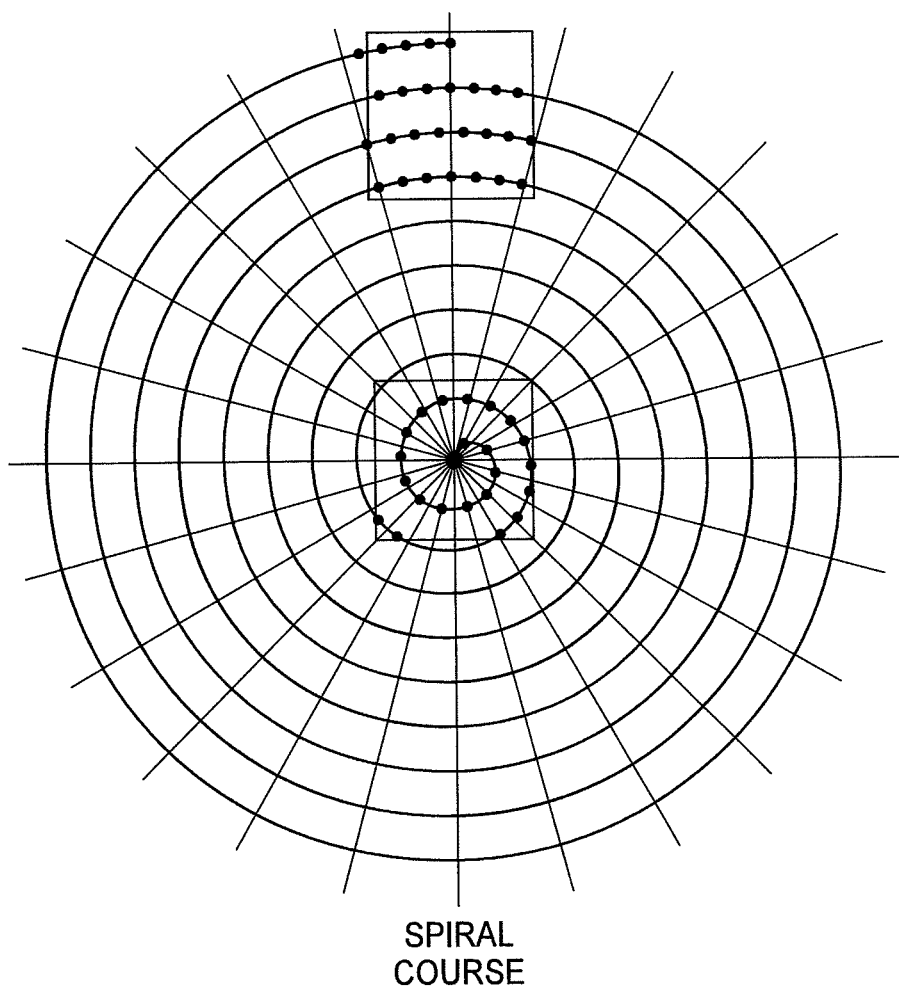
FIG. 10 is a conceptual illustration of the generation cycle of the pixel signals of the embodiment

On the other hand, in the above embodiment, because the A/D conversion cycle is adjusted to be inversely proportional to the distance between the standard point and the position of the emission end, a space between the neighboring sampling points can be held constant. Accordingly, as shown in FIG. 10, the generation density can be kept constant regardless of the distance between the standard point and the position of the emission end.

Consequently, in the above embodiment, since useless pixel signals that would have been deleted without being stored are not generated, power consumption is reduced.

The A/D conversion cycle is adjusted to be inversely proportional to the distance between the standard point and the position of the emission end as the emission end is moved at the constant angular velocity in the above embodiment. However, the angular velocity may be adjusted to be inversely proportional to the distance between the standard point and the position of the emission end as the A/D conversion cycle is kept constant.

Or the angular velocity of the emission end moving along the spiral course and the A/D conversion cycle may both be adjusted so that the product of the angular velocity, the cycle, and the distance between the standard point and the position of the emission end is kept constant.

Or the product of the angular velocity, the cycle, and the distance may not be held completely constant. If the product of the angular velocity "ω1", the cycle "t1", and the distance "r1" when the emission end is farthest from the standard point is smaller than the product (first value) of "r1", the angular velocity and the cycle when the emission end is at the standard point, the number of pixel signals that will be deleted without being stored can be reduced compared to the constant angular velocity and cycle.

The white laser beam is shined on the observation area and a pixel signal is generated according to the amount of light reflected from the illuminated point, in the above embodiment. However, any bands of light that are detectable by a photoelectric converter can be shined on the observation area and the reflected light can be captured. Or excitation light, which makes an organ autofluoresce, can be shined on the observation area and a pixel signal can be generated according to the amount of the resulting autofluorescence.

Lasers are used as light sources to emit red, green, and blue light, in the above embodiment. However, other kinds of light sources may be used. Nevertheless, a laser is the preferable light source in the above embodiment because of its ability to shine illumination light with strong directivity on a minute point within an observation area of the scanning endoscope.

The PMTs are used in the generation of the pixel signals in the above embodiment. However, another kind of a photoelectric converter that can detect the amount of components in light, such as a photodiode, can also be used.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2008-324225 (filed on Dec. 19, 2008), which is expressly incorporated herein, by reference, in its entirety.

The invention claimed is:

1. A scanning endoscope processor, the scanning endoscope processor controlling a scanning endoscope having a first transmitter, an actuator, and a second transmitter, the scanning endoscope processor comprising:
   a photoelectric converter that receives light transmitted from the second transmitter and generates a pixel signal according to the amount of light received, the second transmitter transmitting reflected light and/or fluorescence from a point within an observation area illuminated by the light emitted from a first emission end, the first transmitter transmitting light from a first incident end to the first emission end, the first transmitter emitting the light as a beam from the first emission end, the actuator moving the first emission end along a spiral course, and
   a controller that adjusts a first angular velocity and a generation cycle so that the multiplication product of the first angular velocity, the generation cycle, and a first distance is within a predetermined range, the first emission end being vibrated along first and second diameter directions which are perpendicular to each other and perpendicular to an axial direction of the first emission end such that the first emission end is moved at the first angular velocity along the spiral course, the generation cycle being a cycle for generating the pixel signal, the first distance being a distance between the position of the first emission end on the spiral course and the center of the spiral course.

2. A scanning endoscope processor according to claim 1, wherein the controller adjusts the first angular velocity and the generation cycle so that the multiplication product of the first angular velocity, the generation cycle, and the first distance is kept at a first value, the first value being constant within the predetermined range.

3. A scanning endoscope processor according to claim 1, wherein the controller holds the first angular velocity constant and adjusts the generation cycle.

4. A scanning endoscope processor according to claim 1, wherein the controller holds the generation cycle constant and adjusts the first angular velocity.

5. A scanning endoscope apparatus comprising:
   a first transmitter that transmits light from a first incident end to a first emission end, the first transmitter emitting the light as a beam from the first emission end;
   an actuator that moves the first emission end along a spiral course;
   a second transmitter that transmits reflected light and/or fluorescence from a point within an observation area illuminated by the light emitted from the first emission end;
   a photoelectric converter that receives the light transmitted from the second transmitter and generates a pixel signal according to the amount of the light received; and
   a controller that a first angular velocity and a generation cycle so that the multiplication product of the first angular velocity, the generation cycle, and a first distance is within a predetermined range, the first emission end being vibrated along first and second diameter directions which are perpendicular to each other and perpendicular to an axial direction of the first emission end such that the first emission end is moved at the first angular velocity along the spiral course, the generation cycle being a cycle for generating the pixel signal, the first distance being a distance between the position of the first emission end on the spiral course and the center of the spiral course.

* * * * *